United States Patent [19]

Weiner et al.

[11] Patent Number: 5,643,326
[45] Date of Patent: Jul. 1, 1997

[54] DUAL CHAMBER PACING WITH ATRIAL AND VENTRICULAR INDEPENDENCE

[76] Inventors: Henry L. Weiner, 1 Sommerset La., Newark, Del. 19711; H. Toby Markowitz, 1670 Ridgewood La. South, Roseville, Minn. 55113; Michael F. Hess, 3841 Pleasant La. South, Minneapolis, Minn. 55409

[21] Appl. No.: 568,440

[22] Filed: Dec. 7, 1995

Related U.S. Application Data

[63] Continuation of Ser. No. 250,216, May 27, 1994, abandoned.

[51] Int. Cl.⁶ .................................................. A61N 1/368
[52] U.S. Cl. ........................................ 607/14; 607/9; 607/17
[58] Field of Search .................................. 607/9, 14, 17

[56] References Cited

U.S. PATENT DOCUMENTS 5,133,350  7/1992  Duffin .

FOREIGN PATENT DOCUMENTS

| 0401962 | 12/1990 | European Pat. Off. . |
|---|---|---|
| 0488904 | 6/1992 | European Pat. Off. . |
| 0494487 | 7/1992 | European Pat. Off. . |
| 0590275 | 4/1994 | European Pat. Off. . |
| 0590276 | 4/1994 | European Pat. Off. . |
| 0624386 | 11/1994 | European Pat. Off. . |
| 8203781 | 11/1982 | WIPO . |
| 9213595 | 8/1992 | WIPO . |
| 9216258 | 10/1992 | WIPO . |

*Primary Examiner*—William E. Kamm
*Assistant Examiner*—Kennedy J. Schaetzle
*Attorney, Agent, or Firm*—Michael B. Atlass; Harold R. Patton

[57] ABSTRACT

A rate-responsive cardiac pacemaker implements a novel pacing mode, identified as ADIR/VVIR, which is especially effective for patients with Sick Sinus Syndrome and only intermittent atrioventricular block. Within the same pacemaker circuitry, an AAIR pacemaker and a VVI pacemaker (with an escape rate below that of the AAIR pacemaker) are provided with atrial blanking following both atrial and ventricular events. Ventricular blanking after atrial pacing is minimized for better detection of R-waves following an atrial paced event.

28 Claims, 5 Drawing Sheets

DUAL CHAMBER PACING WITH ATRIAL AND VENTRICULAR INDEPENDENCE

This application is a continuation of application Ser. No. 08/250,216 filed on May 27, 1994 and abandoned in favor hereof.

FIELD OF THE INVENTION

The present invention relates to artificial cardiac pacemakers, and the treatment of patients with Sick Sinus Syndrome and primarily intact atrioventricular conduction.

BACKGROUND OF THE INVENTION

Generally speaking, a cardiac pacemaker or implantable pulse generator (IPG) is an electrical device used to supplant some or all of an abnormal heart's natural pacing function, by delivering appropriately timed electrical stimulation signals designed to cause the myocardium of the heart to contract or "beat".

Current pacing modes are well-suited for patients with atrioventricular (AV) block. That is, loss of function in the AV node, resulting in loss of electrical conduction between the atria and ventricles.

Some pacemaker patients who have Sick Sinus Syndrome (SSS) have intact AV conduction most of the time, but may be subject to an occasional AV block. For such a patient, the AAIR pacing mode (the pacemaker paces in atrium, senses in atrium, is inhibited in response to a sensed beat, and is rate responsive) is not adequate since the ventricles need to be paced during AV block. Another pacing mode, DDIR (the pacemaker paces in both chambers, senses in both chambers, is inhibited in response to sensed beats, and is rate responsive) solves some of the problems associated with the AAIR mode, but requires adjustments of the AV intervals (time between atrial and ventricular depolarization) and the post ventricular atrial refractory period (PVARP) in order to preserve AV conduction and prevent "competitive" pacing.

SUMMARY OF THE INVENTION

In view of the foregoing, it is a first object of the present invention to provide a cardiac pacemaker capable of AAIR-style pacing, yet still capable of ventricular pacing during AV block.

It is a second object of the present invention to provide a cardiac pacemaker capable of meeting the above object, yet eliminating the possibility of competitive atrial pacing.

It is a third object of the present invention to provide a cardiac pacemaker capable of meeting the above objects, and capable of pacing the ventricles in ventricular pace and sense modes during atrial flutter and atrial fibrillation.

In order to satisfy the above objects and others, the present invention provides a dual chamber, rate-responsive cardiac pacemaker capable of operating in a novel "ADIR/VVIR" pacing mode. The pacemaker at least includes: an atrial pacemaker; a ventricular pacemaker with a ventricular lower (escape) rate below the atrial lower (escape) rate of the atrial pacemaker; control means coupled to the atrial and ventricular pacemakers to control their operation; and atrial blanking means coupled to the atrial pacemaker and to the control means for introducing blanking to the atrial pacemaker after an atrial or ventricular event.

The present invention further provides a novel cardiac pacing method (ADIR/VVIR mode) adapted for use by a dual chamber, rate-responsive cardiac pacemaker at least including the steps of: pacing an atrium with an atrial pacemaker; pacing a ventricle with a ventricular pacemaker having a ventricular lower (escape) rate below the atrial lower (escape) rate of the atrial pacemaker; controlling the operation of the atrial and ventricular pacemakers with a control means; and introducing blanking to the atrial pacemaker after an atrial or ventricular event.

The details of the present invention will be revealed in the following description, with reference to the drawing.

BRIEF DESCRIPTION OF THE DRAWING

The various figures of the drawing are briefly described as follows.

DETAILED DESCRIPTION OF THE INVENTION

Part I. Elementary Description

Figure 1:
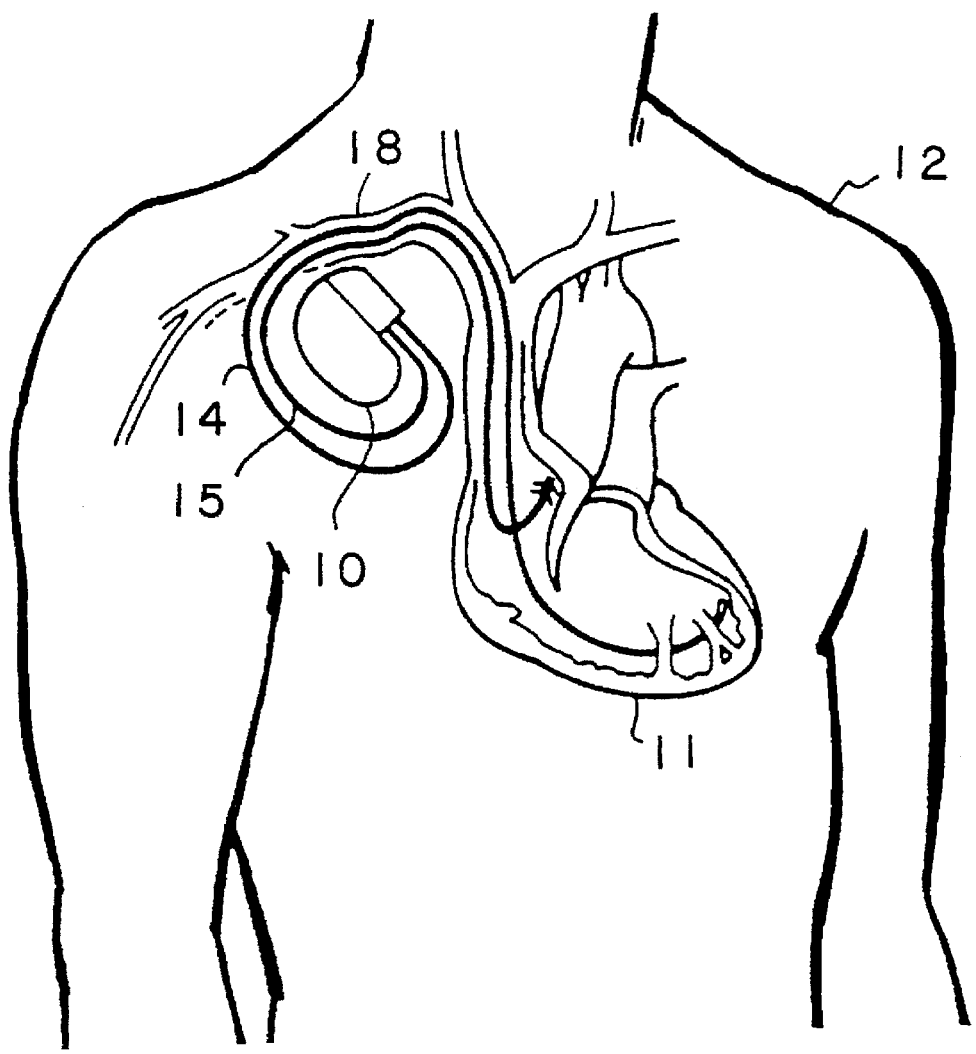
FIG. 1 is a diagram showing the heart of a patient electrically connected to the pacemaker in FIG. 2.

FIG. 1 generally shows a pacemaker 10 implanted in a patient 12. The pacemaker leads 14 and 15 electrically couple the pacemaker 10 to the patient's heart 11 via a suitable vein 18. The leads act to both sense polarizations in the heart, and to deliver pacing stimuli the heart.

Part II. General Description of the Pacemaker Device

Figure 2:
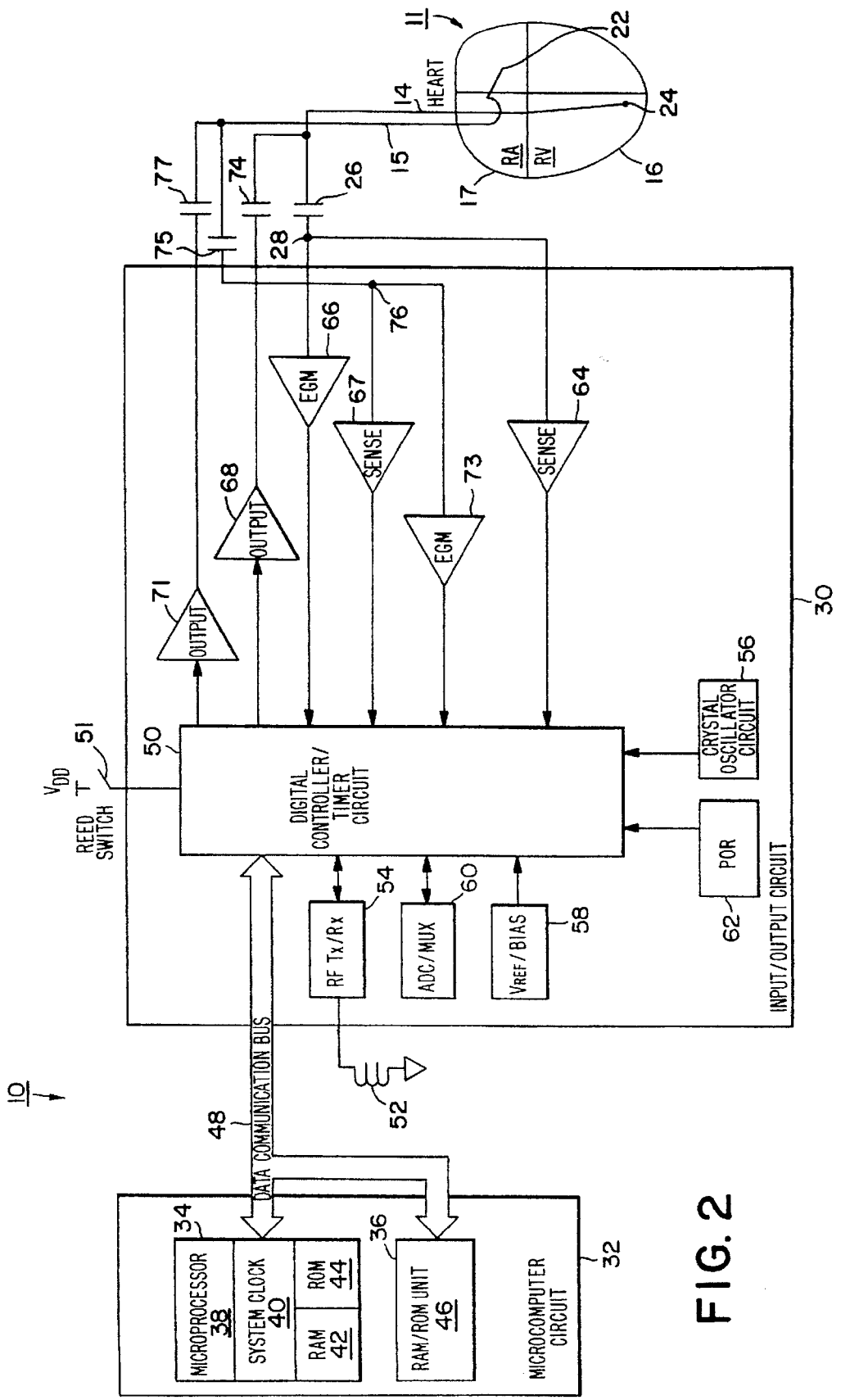
FIG. 2 is a schematic block diagram of a multi-sensor, rate-responsive, dual chamber implantable pulse generator (IPG) capable of subsuming the present invention.

FIG. 2 is a block circuit diagram illustrating a multi-programmable, implantable, dual-chamber, bradycardia pacemaker 10 capable of carrying out the present invention. Although the present invention is described in conjunction with a microprocessor-based architecture, it will be understood by those skilled in the art that it could be implemented in other technology such as digital logic-based, custom integrated circuit (IC) architecture, if desired. It will also be understood that the present invention may be implemented in cardioverters, defibrillators and the like.

Lead 14 includes an intracardiac electrode 24 located near its distal end and positioned within the right ventricle 16. Electrode 24 is coupled by a lead conductor 14 through an input capacitor 26 to the node 28, and to the input/output terminals of an input/output circuit 30.

Similarly, the lead 15 has a distally located intracardiac electrode positioned within the right atrium 17. Electrode 22 is coupled by a lead conductor 15 through an input capacitor 75 to a node 76, and to the input/output terminals of the input/output circuit 30.

Input/Output Circuit 30 contains the operating input and output analog circuits for digital controlling and timing circuits necessary for the detection of electrical signals derived from the heart, such as the cardiac electrogram, output from sensors (not shown) connected to the leads 14 and 15, as well as for the application of stimulating pulses to the heart to control its rate as a function thereof under the control of software-implemented algorithms in a Microcomputer Circuit 32.

Microcomputer Circuit 32 comprises an On-Board Circuit 34 and an Off-Board Circuit 36. On-Board Circuit 34 includes a microprocessor 38, a system clock 40, and on-board RAM 42 and ROM 44. Off-Board Circuit 36 includes an off-board RAM/ROM Unit 46. Microcomputer Circuit 32 is coupled by Data Communication Bus 48 to a Digital Controller/Timer Circuit 50. Microcomputer Circuit 32 may be fabricated of custom IC devices augmented by standard RAM/ROM components.

It will be understood by those skilled in the art that the electrical components represented in FIG. 2 are powered by an appropriate implantable-grade battery power source (not shown).

An antenna 52 is connected to Input/Output Circuit 30 for purposes of uplink/downlink telemetry through a radio frequency (RF) Transmitter/Receiver Circuit (RF TX/RX) 54. Telemetering both analog and digital data between antenna 52 and an external device, such as an external programer (not shown), is accomplished in the preferred embodiment by means of all data first being digitally encoded and then pulse position modulated on a damped RF carrier, as substantially described in U.S. Pat. No. 5,127,404, issued on Jul. 7, 1992, entitled "Telemetry Format for Implantable Medical Device", which is held by the same assignee as the present invention and which is incorporated herein by reference. A reed switch 51 is connected to Input/Output Circuit 30 to enable patient follow-up via disabling the sense amplifier 146 and enabling telemetry and programming functions, as is known in the art.

A Crystal Oscillator Circuit 56, typically a 32,768 Hz crystal-controlled oscillator, provides main timing clock signals to Digital Controller/Timer Circuit 50. A Vref/Bias Circuit 58 generates a stable voltage reference and bias currents for the analog circuits of Input/Output Circuit 30. An ADC/Multiplexer Circuit (ADC/MUX) 60 digitizes analog signals and voltages to provide telemetry and a replacement time-indicating or end-of-life function (EOL). A Power-on-Reset Circuit (POR) 62 functions to initialize the pacemaker 10 with programmed values during power-up, and reset the program values to default states upon the detection of a low battery condition or transiently in the presence of certain undesirable conditions such as unacceptably high electromagnetic interference (EMI), for example.

The operating commands for controlling the timing of the pacemaker depicted in FIG. 2 are coupled by bus 48 to Digital Controller/Timer Circuit 50 wherein digital timers set the overall escape interval of the pacemaker, as well as various refractory, blanking and other timing windows for controlling the operation of the peripheral components within Input/Output Circuit 50.

Digital Controller/Timer Circuit 50 is coupled to sense amplifiers (SENSE) 64 and 67, and to electrogram (EGM) amplifiers 66 and 73 for receiving amplified and processed signals picked up from electrode 24 through lead 14 and capacitor 26, and for receiving amplified and processed signals picked up from electrode 22 through lead 15 and capacitor 75, representative of the electrical activity of the patient's ventricle 16 and atrium 17, respectively. Similarly, SENSE amplifiers 64 and 67 produce sense event signals for re-setting the escape interval timer within Circuit 50. The electrogram signal developed by EGM amplifier 66 is used in those occasions when the implanted device is being interrogated by the external programmer/transceiver (not shown) in order to transmit by uplink telemetry a representation of the analog electrogram of the patient's electrical heart activity as described in U.S. Pat. No. 4,556,063, issued to Thompson et al., entitled "Telemetry System for a Medical Device", which is held by the same assignee as the present invention, and which is incorporated herein by reference.

Output pulse generators 68 and 71 provide the pacing stimuli to the patient's heart 11 through output capacitors 74 and 77 and leads 14 and 15 in response to paced trigger signals developed by Digital Controller/Timer Circuit 50 each time the escape interval times out, or an externally transmitted pacing command has been received, or in response to other stored commands as is well known in the pacing art.

In a preferred embodiment of the present invention, pacemaker 10 is capable of operating in various non-rate-responsive modes which include DDD, DDI, VVI, VOO and VVT, as well as corresponding rate-responsive modes of DDDR, DDIR, VVIR, VOOR and VVTR. Further, pacemaker 10 can be programmably configured to operate such that it varies its rate only in response to one selected sensor output, or in response to both sensor outputs, if desired.

Part III. ADIR/VVIR Mode Operation

Details of the ADIR/VVIR mode of the present invention follow below, with reference to FIGS. 3 through 9. In those figures the following abbreviations are used to indicate the occurrence of cardiac events: AS for atrial sense; AP for atrial pace; VS for ventricular sense; and VP for ventricular pace. The pacemaker 10 operates as a combination of a separate AAIR pacemaker for the atrial channel, and a separate VVIR pacemaker for the ventricular channel. Atrial blanking follows both atrial and ventricular events, with the blanking period equal to approximately 180 ms when the ventricular event is either paced or premature, and approximately 120 ms at the start of an orthodromically conducted ventricular beat. The blanking periods may be different from the above numbers, according to the needs of the patient, etc.

The lower rate of the ventricular pacemaker is lower than the lower rate of the atrial pacemaker so that ventricular pacing occurs only during episodes of AV block. In addition to AV block, the patient must also experience atrial arrhythmias (i.e., flutter, fibrillation) in order for the ventricular pacemaker to be activated. Thus, in cases of AV block, but sinus rhythm, the pacemaker 10 switches to a fully automatic mode, which includes such modes as DDDR, DDDR with, DDIR, VVIR, etc. Table 1 summarizes the operation of the pacemaker 10 under various conditions.

TABLE 1

SUMMARY OF ADIR/VVIR PACEMAKER OPERATION

| Condition | Result |
| --- | --- |
| 1. AV conduction | AAIR activated; VVIR sensing only |
| 2. Sinus rhythm with AV block | Pacemaker switches to DDDR operation |

TABLE 1-continued

SUMMARY OF ADIR/VVIR PACEMAKER OPERATION

| Condition | Result |
| --- | --- |
| 3. Atrial Arrhythmia, no AV block | VVI activated |
| 4. Atrial Arrythmia with AV block | VVIR activated |

Figure 3:
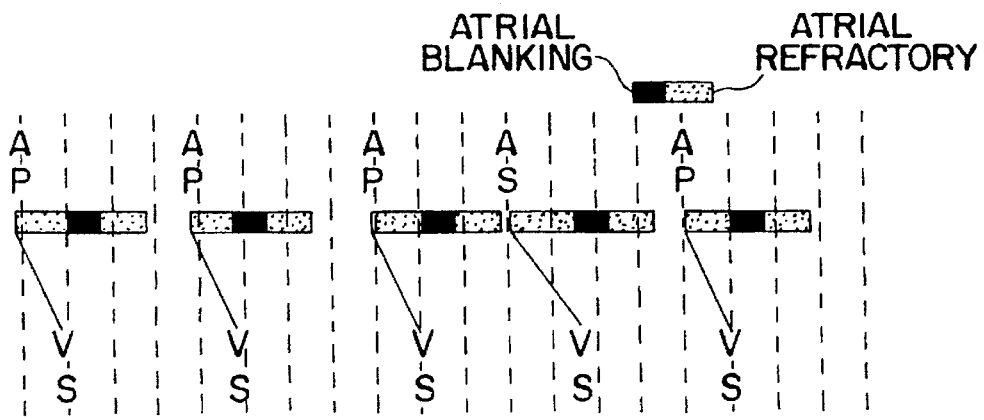
FIG. 3 is a timing diagram with cardiac events during the normal ADIR/VVIR operation of the present invention.

FIG. 3 is a timing diagram illustrating condition 1 in Table 1, supra. During normal operation with AV conduction, the atrial pacemaker is enabled while the ventricular pacemaker is disabled (i.e., the only function of the ventricular pacemaker in this case is to monitor ventricular sense events). An atrial refractory period starts at the beginning of each atrial event. The pacemaker 10 uses atrial-to-atrial (A-A) timing to determine the escape interval. At the detection of a ventricular event (sense in this case) the atrial pacemaker begins an atrial blanking period (120 ms in the preferred embodiment) followed by an atrial refractory period.

Figure 4:
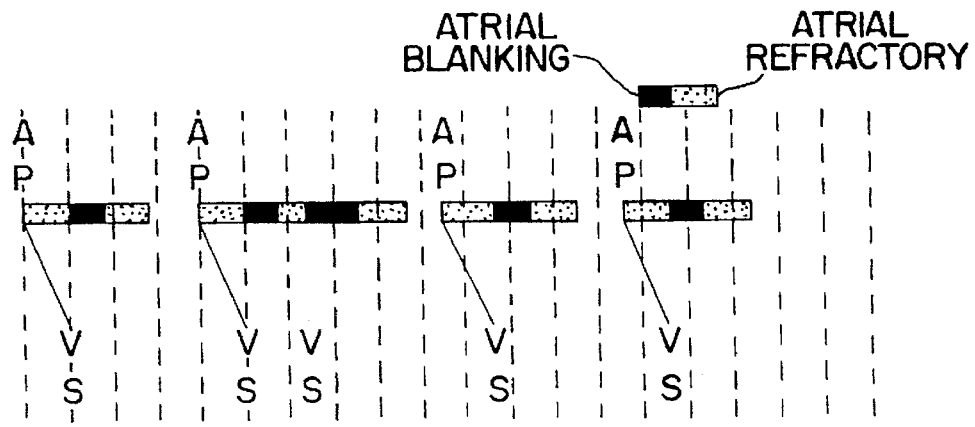
FIG. 4 is a timing diagram with cardiac events including a premature ventricular contraction during the ADIR/VVIR mode of the present invention.

FIG. 4 illustrates the operation of the pacemaker 10 after the occurrence of a premature ventricular contraction (PVC), a ventricular sense event occurring without an intervening atrial event since the last ventricular event. At the occurrence of a PVC (the third ventricular sense event shown) the longer atrial blanking period starts (180 ms), and the atrial pacemaker is reset to pace after the expiration of the current A-A interval minus the intrinsic conduction time of the patient as measured by the pacemaker. This reset delay period is hereby referred to as the "pseudo" V-A interval.

Figure 5:
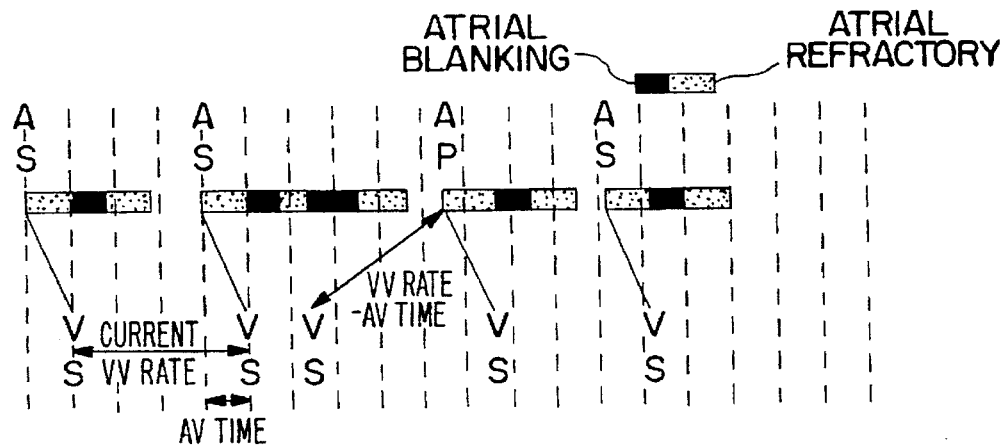
FIG. 5 is a timing diagram with cardiac events illustrating the rate smoothing feature of the present invention.

FIG. 5 illustrates an alternate approach to a PVC involving rate smoothing to minimize ventricular rate drops. In this approach the pseudo V-A interval used to reset the atrial pacemaker equals the current ventricular-to-ventricular (V-V) interval minus the intrinsic conduction time.

Figure 6:
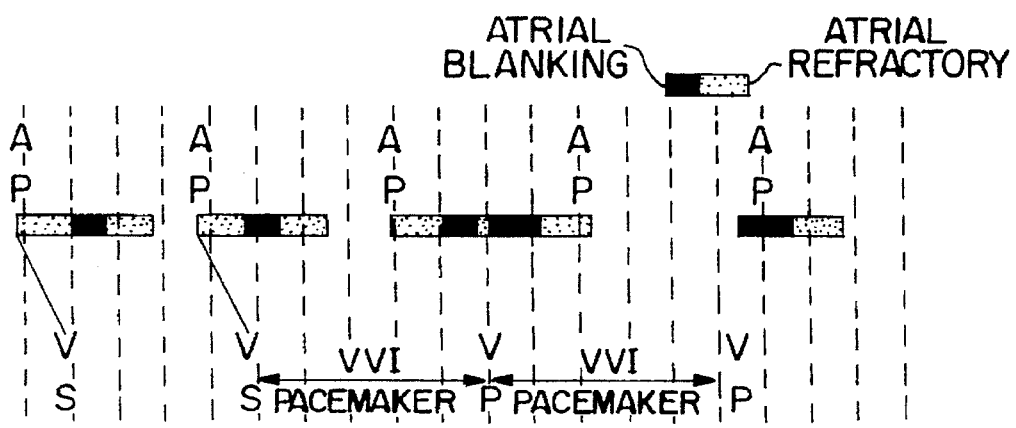
FIG. 6 is a timing diagram of the present invention showing cardiac events during an AV block episode.

FIG. 6 illustrates the pacemaker's ADIR/VVIR operation during the presence of atrial arrhythmia and intermittent AV block. As will be appreciated by those skilled in the art, numerous references discuss methods for detecting arrhythmias. One such reference is an article entitled "Automatic Tachycardia Recognition" by Robert Arzbaecher et al., PACE 7 (1984) 541-547, hereby incorporated by reference. Another reference is U.S. Pat. No. 4,880,005 issued to Benjamin D. Pless et al. on Nov. 14, 1989 for "PACEMAKER FOR DETECTING AND TERMINATING A TACHYCARDIA," which is also incorporated by reference.

During the first two cardiac cycles shown, the atrial paces are conducted normally to the ventricles, thus inhibiting the ventricular pacemaker. In the third and fourth cardiac cycles, however, AV block triggers the ventricular pacemaker, causing it to pace the ventricle at the expiration of the ventricular escape interval. Recall that atrial blanking and atrial refractory periods follow each ventricular event (when the ventricular event is paced the blanking period equals 180 ms in the preferred embodiment).

Figure 7:
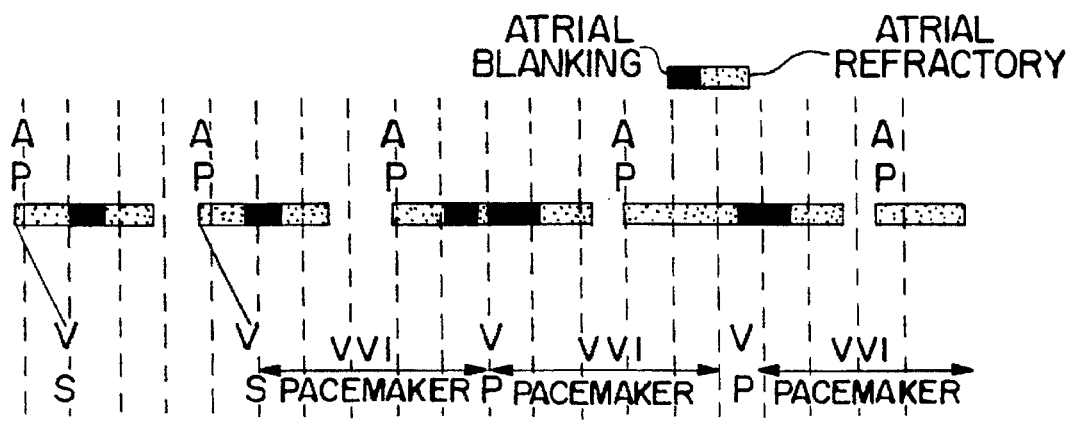
FIG. 7 is a timing diagram of the present invention including reset of the atrial pacemaker following a ventricular escape pace.

In the above example, a potential exists for retrograde conduction of ventricular pace events, which is undesirable. To eliminate this problem, the atrial pacemaker is reset following a ventricular pace (at expiration of the ventricular escape interval) as shown in FIG. 7. The pseudo V-A interval is chosen to be either the current A-A escape interval minus the intrinsic conduction time as described in conjunction with FIG. 4, or the current ventricular rate minus the AV interval as described in conjunction with FIG. 5.

Figure 8:
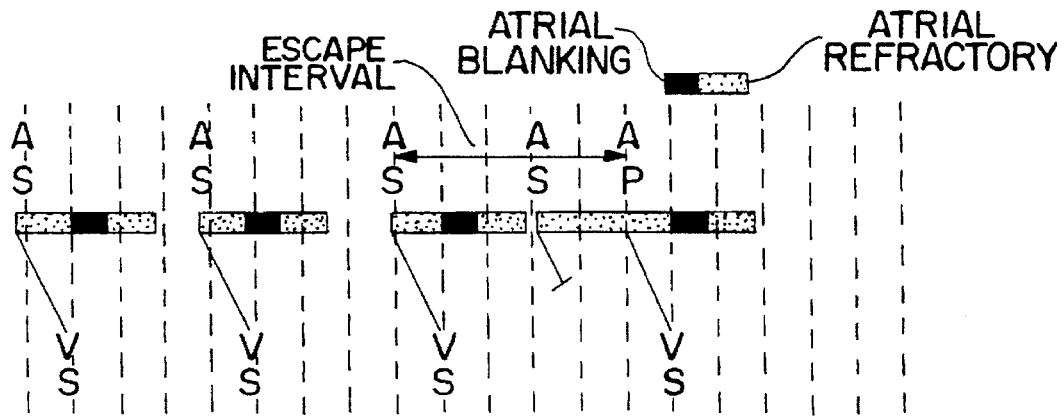
FIG. 8 is a timing diagram of the present invention illustrating the response to a non-conducted premature atrial contraction.

FIG. 8 illustrates the response of the pacemaker 10 to a non-conducted premature atrial contraction (PAC). After the third cardiac cycle in the illustration, an atrial sense event occurs during the atrial refractory period. In order to minimize the drop in ventricular rate after the occurrence of a non-conducted PAC, the atrial escape interval is timed not from the PAC, but from the previous atrial event. In order to determine that a PAC has not conducted, the pacemaker must wait for the AV interval plus a predefined interval unique to the delay in conduction from PACs.

If the PAC is conducted, the atrial escape interval is timed from the PAC. Otherwise, the atrial escape interval is timed from the previous atrial event.

Figure 9:
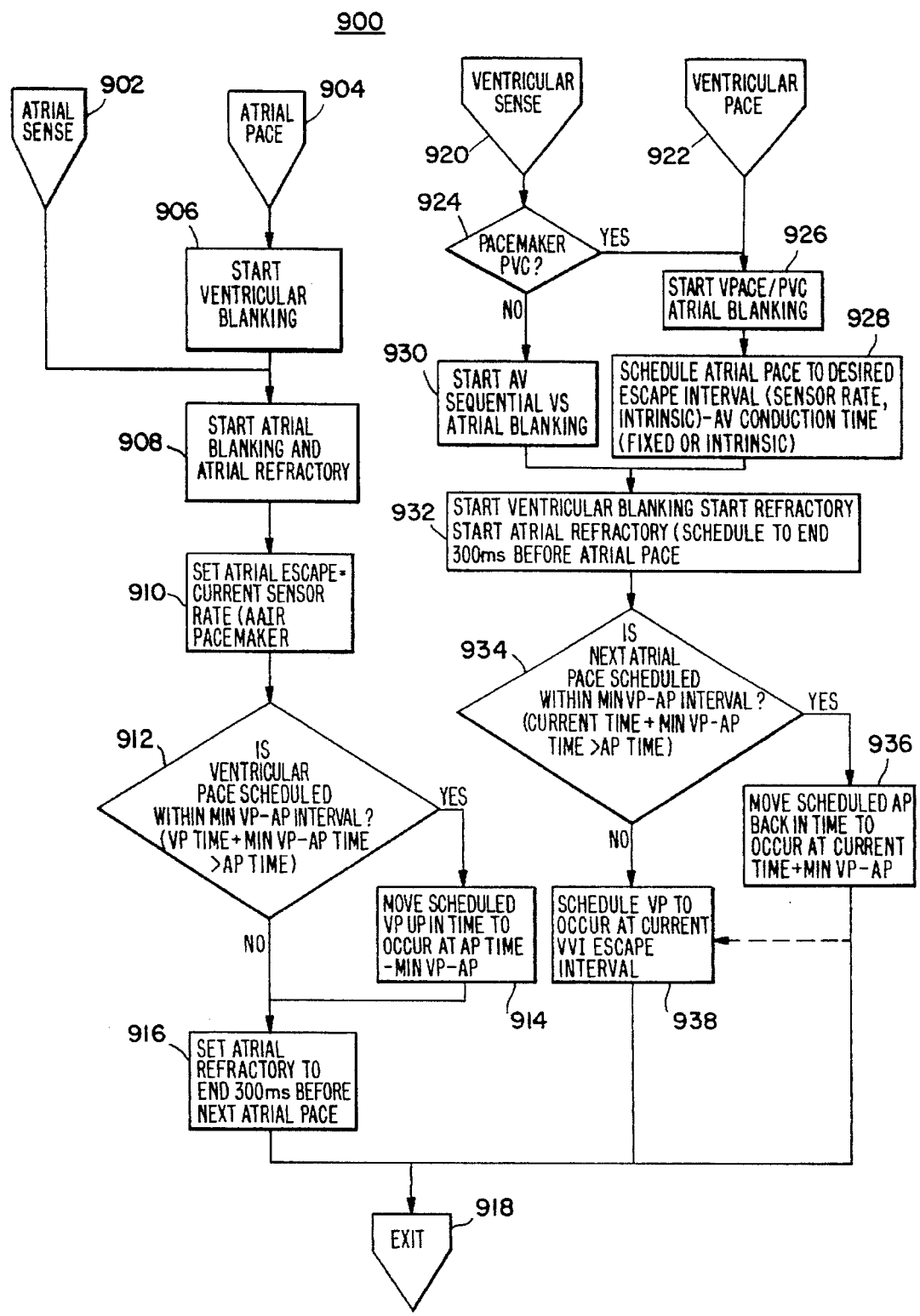
FIG. 9 is a flowchart illustrating the algorithm for implementing the present invention.

FIG. 9 is a flowchart summarizing the procedure/program 900 used by the pacemaker 10 to implement the ADIR/VVIR mode. Steps 902 through 916 describe the operation of the atrial pacemaker, while Steps 920 through 938 describe the operation of the ventricular pacemaker.

Atrial pace events (Step 904) trigger ventricular blanking at Step 906. Both atrial sense events (Step 902) atrial pace events trigger the atrial blanking and atrial refractory periods at Step 908. At Step 910 the atrial escape rate is set equal to the current sensor rate.

The pacemaker 10 determines at Step 912 whether a ventricular pace is scheduled within the programmed minimum ventricular pace (VP)-to-atrial pace (AP) interval (the minimum interval which must occur after a VP before an AP can occur). If the VP is to occur in the minimum VP-AP interval, it is moved up in time to occur at the scheduled AP time minus the minimum VP-AP interval (Step 914). At Step 916 the atrial refractory period is set to end 300 ms before the next scheduled atrial pace event.

Step 918, the last step in the program 900, places the pacemaker 10 in a monitoring mode to await re-triggering of the program by an atrial or ventricular event (Steps 902, 904, 920 or 922).

A ventricular sense event (Step 920) advances the program 400 to Step 924, which determines whether the ventricular event is a PVC. If so, the program advances to Step 930, where a short atrial blanking period is started (i.e., about 120 ms, as described supra.).

At Step 926, whenever a ventricular pace occurs (Step 922), or a PVC, a longer atrial blanking period is started (i.e., about 180 ms, as described supra.). Following a ventricular pace or a PVC the next atrial pace is scheduled to occur after the atrial escape interval minus the AV conduction time (Step 928).

At Step 932 the ventricular blanking and refractory periods are started, as well as the atrial refractory period (the atrial period is set to end 300 ms before the next scheduled atrial pace, as in Step 916).

The pacemaker 10 determines at Step 934 whether the next atrial pace is scheduled within the programmed minimum Ventricular Pace-to-Atrial Pace interval (the minimum interval which must occur after a VP before an AP can occur). If the AP is to occur in the minimum VP-AP interval, it is moved back in time to occur at the scheduled AP time plus the minimum VP-AP interval (Step 936). If the next atrial pace is not scheduled to occur within the minimum VP-AP interval, the next ventricular pace is then scheduled to occur at the current ventricular escape interval (Step 938). The program then advances to Step 918 so that the pacemaker 10 resumes its monitoring mode, as described supra.

Variations and modifications to the present invention are possible given the above disclosure. However, such variations and modifications are intended to be within the scope of the invention claimed by this letters patent.

We claim:

1. A dual chamber, rate-responsive cardiac pacemaker having sensing means for sensing atrial and ventricular events, storage circuitry for holding values for an atrial lower escape interval and a ventricular lower escape interval, said intervals for defining atrial and ventricular escape rates, respectively comprising:

an atrial pacemaker having an atrial lower escape rate;

a ventricular pacemaker with a ventricular lower escape rate below the atrial lower escape rate of said atrial pacemaker;

control means coupled to said atrial and ventricular pacemakers to control their operation; and atrial blanking means coupled to said atrial pacemaker and to said control means for introducing blanking to said atrial pacemaker after an atrial or ventricular event comprising:

first blanking period means for providing a first blanking period following a paced ventricular event or premature ventricular event; and second blanking period means for providing a second blanking period following an orthodromically conducted ventricular event;

wherein said blanking period is shorter than said first blanking period.

2. The cardiac pacemaker in claim 1 further comprising:

atrial arrhythmia determination means for determining atrial arrhythmia coupled to said control means; and a fully automatic rate-responsive pacemaker coupled to said control means;

wherein, after the occurrence of a predetermined number of ventricular paced events, accompanied by atrioventricular block without atrial arrhythmia, said fully automatic pacemaker is enabled, and said atrial and ventricular pacemakers are disabled.

3. The cardiac pacemaker in claim 2 further comprising:

automatic mode switching means coupled to said control means for automatically switching the mode of said fully automatic rate-responsive pacemaker upon the occurrence of predetermined events.

4. The cardiac pacemaker in claim 1 further comprising:

atrial pacemaker reset means for resetting said atrial pacemaker after a ventricular escape pace.

5. The cardiac pacemaker in claim 4 wherein the ventricular-to-atrial interval after a ventricular escape pace equals the atrial pacemaker's current atrial-to-atrial escape interval minus a patient's intrinsic conduction time.

6. The cardiac pacemaker in claim 4 wherein the ventricular-to-atrial interval after a ventricular escape pace equals the ventricular pacemaker's current ventricle-to-ventricle rate minus a patient's intrinsic conduction time.

7. The cardiac pacemaker in claim 1 further comprising:

premature atrial contraction determination means for determining the occurrence of a premature atrial contraction;

wherein the atrial escape interval of said atrial pacemaker is timed from the occurrence of the said premature atrial contraction when it is conducted to the ventricle, and said atrial escape interval is timed from the atrial event previous to the premature atrial contraction when the premature atrial contraction is not conducted to the ventricle.

8. A cardiac pacing method adapted for use by a dual chamber, rate-responsive cardiac pacemaker comprising the steps of:

pacing an atrium with an atrial pacemaker;

pacing a ventricle with a ventricular pacemaker having a ventricular lower escape rate below the atrial lower escape rate of said atrial pacemaker;

controlling the operation of said atrial and ventricular pacemakers with a control means and introducing blanking to said atrial pacemaker after an atrial or ventricular event by a) providing a first blanking period following a paced ventricular event or premature ventricular event; and b) providing a second blanking period shorter than said first blanking period following an orthodromically conducted ventricular event.

9. The cardiac pacing method in claim 8 further comprising, after the occurrence of a predetermined number of ventricular paced events, accompanied by atrioventricular block without atrial arrhythmia:

pacing said atria and ventricles with a fully automatic rate-responsive pacemaker; and disabling said atrial and ventricular pacemakers.

10. The cardiac pacing method in claim 9 further comprising the step of:

automatically switching the mode of said fully automatic rate-responsive pacemaker upon the occurrence of predetermined events.

11. The cardiac pacing method in claim 8 further comprising the step of:

resetting said atrial pacemaker after a ventricular escape pace.

12. The cardiac pacing method in claim 11 wherein the ventricular-to-atrial interval after a ventricular escape pace equals the atrial pacemaker's current atrial-to-artial escape interval minus a patient's intrinsic conduction time.

13. The cardiac pacing method in claim 11 wherein the ventricular-to-atrial interval after a ventricular escape pace equals the ventricular pacemaker's current ventricle-to-ventricle rate minus a patient's intrinsic conduction time.

14. The cardiac pacing method in claim 8 further comprising the steps of:

determining the occurrence of a premature atrial contraction;

timing the atrial escape interval of said atrial pacemaker from the occurrence of the said premature atrial contraction when it is conducted to the ventricle; and timing said atrial escape interval from the atrial event previous to the premature atrial contraction when the premature atrial contraction is not conducted to the ventricle.

15. An implantable cardiac pulse generator(10) (also called an IPG) having stimulating electrical pulse delivery leads (14, 15) for placement in an atrium (17) and a ventricle (16) and capable of sensing atrial and ventricular depolarizations and of establishing timing intervals based on individual senses of said depolarizations characterized in that said IPG is adapted to pace the atrium to compensate for sick sinus syndrome and to pace the ventricle in the event ventricular pacing is also needed, and also adapted to be rate responsive to sensed patient activity via an activity sensor the output of which is used to establish a sensor rate interval, wherein said IPG is characterized in that it comprises:

storage circuitry for storing values related to the timing intervals including at least V-V and A-A escape interval values a VA minimum value;

two independent control processes(32), a vcm and an acm within said IPG both connected (67,64,73) to receive signals indicative of said ventricular (920) and atrial depolarizations (902)and based on the timing of said depolarizations deliver ventricular and atrial stimulating pulses, respectively such that, said vcm is a ventricular pulse delivery lead control process, adapted to be responsive to expiry of said V-V escape interval (938) for causing to be delivered (922)a ventricular stimulating pulse (VP) at the expiry of said V-V escape interval, and said acm is an atrial pulse delivery lead control process adapted to be responsive to expiry of said A-A escape interval(910), for causing to be delivered (904) an atrial stimulating pulse (AP) at the expiry of said A-A escape interval, and wherein timing of delivery of said stimulation pulses by the two processes is related to a minimum VA interval value (912,913,934,936) and its predetermined relationship to current values in said storage circuitry for said V-V (938)and A-A (910)escape intervals.

16. An IPG as set forth in claim 15 wherein the V-V escape interval value is related to the minimum VA interval value by the relation: V-V escape interval=the minimum of either: a Ventricular Lower Rate Interval, or the VA escape interval+a sensor rate interval–the minimum VA interval.

17. An IPG as set forth in claim 15 wherein the A-A interval is related to the minimum VA interval by the relation: A-A escape interval=activity sensor interval or the VA interval, whichever is larger.

18. An IPG as set forth in claim 15 further comprising means to initiate blanking periods for atrial and ventricular event sensors which produce said indications of atrial and ventricular depolarizations, respectively, wherein after delivery of an atrial stimulating pulse and also after a sensed atrial depolarization an atrial refractory and an atrial blanking period are started, and a ventricular blanking period is started after an atrial pace.

19. An IPG as set forth in claim 15 further comprising means to initiate blanking periods for atrial and ventricular event sensors which produce said indications of atrial and ventricular depolarizations, respectively, and having means for determining if a ventricular depolarization is a premature ventricular contraction called a PVC, wherein a ventricular blanking, an atrial refractory and a ventricular refractory period are started after either a ventricular sense or pace and wherein atrial blanking for PVC and ventricular pacing are also started after a sensed PVC or a ventricular pace.

20. An IPG as set forth in claim 15 wherein a VA interval timer is reset after a ventricular escape pace.

21. A method for operating an implantable cardiac pulse generator (also called an IPG) having stimulating electrical pulse delivery leads adapted for placement in an atrium and a ventricle and capable of sensing atrial and ventricular depolarizations characterized in that said method is adapted to pace the atrium and the ventricle in the event ventricular pacing is also needed, and also being rate responsive to sensed patient activity via an activity sensor output signals from which are measured and used to establish a sensor rate interval, wherein said method is characterized in that it comprises:

sensing atrial and ventricular depolarizations relative timing and activity sensor rate interval values to determine a minimum VA interval, pacing the atrium at the expiry of an A-A interval, pacing the ventricle at the expiry of a V-V interval, and upon pacing the ventricle, resetting the VA interval.

22. The method of claim 21 further characterized in that said A-A interval is defined by the measurement of the patient activity based on said activity sensor.

23. The method of claim 22 further characterized in that the A-A interval is defined as the slower of the activity sensor defined rate or said minimum VA interval defined rate.

24. The method of claim 21 further characterized in that the V-V interval is related to the minimum VA interval by the relation: V-V interval=the minimum of either the V-V interval, or the VA interval plus the Sensor Rate interval–the minimum VA interval.

25. The method of claim 21 further characterized in that the A-A interval is related to the minimum VA interval by the relation: A-A interval=activity sensor interval or the VA interval, whichever is larger.

26. The method of claim 21 further characterized in that after delivery of an atrial stimulating pulse and also after a sensed atrial depolarization an atrial refractory and an atrial blanking period are started, and a ventricular blanking period is started after an atrial pace.

27. The method of claim 21 further characterized in that a ventricular blanking, an atrial refractory and a ventricular refractory period are started after either a ventricular sense or pace and wherein atrial blanking for PVC and ventricular pacing are also started after a sensed PVC or a ventricular pace.

28. The method of claim 21 further characterized in that said VA interval is reset after a ventricular escape pace.

* * * * *